United States Patent [19]

Langer et al.

[11] Patent Number: 5,113,010

[45] Date of Patent: May 12, 1992

[54] PROCESS FOR SYNTHESIZING 4,4'-BIS(CARBOALKOXYSTILBENE) DERIVATIVES

[75] Inventors: Matthew E. Langer, New City, N.Y.; Ferial Khorshahi, Leonia, N.J.

[73] Assignee: Lever Brothers Company, Division of Conopco, Inc., New York, N.Y.

[21] Appl. No.: 626,086

[22] Filed: Dec. 11, 1990

[51] Int. Cl.$^5$ .............................. C07C 67/343
[52] U.S. Cl. ...................... 560/96; 560/76; 562/488
[58] Field of Search ............ 560/96, 76; 562/488

[56] References Cited

U.S. PATENT DOCUMENTS 4,537,985 8/1985 Puskas et al. .................. 560/96
4,713,472 12/1987 Van Sicle et al. ............... 560/53
4,789,755 12/1988 Van Sickle et al. ............. 560/78
4,798,911 1/1989 Lentz et al. .................... 568/747

OTHER PUBLICATIONS

Heitz et al., *Makramol Chem.*, 189 (i): 119–127 (1988).
B. H. Lee et al., *J. Polymer Sci., Polym. Chem. Ed.* 20:393–399, (1982).

*Primary Examiner*—Jose G. Dees
*Assistant Examiner*—Vera C. Clarke
*Attorney, Agent, or Firm*—Ronald A. Koatz

[57] ABSTRACT

The invention is concerned with a novel route for making 4,4'-bis(carboalkoxystilbene) derivatives. The process involved is a variation of the Wittig process and allows the compound to be obtained in a less costly and safer way.

8 Claims, No Drawings

PROCESS FOR SYNTHESIZING 4,4'-BIS(CARBOALKOXYSTILBENE) DERIVATIVES

FIELD OF THE INVENTION

1. Field of the Invention

This invention relates to an improved process for 4,4'-bis(carboalkoxystilbene) derivatives and in particular, a process for synthesizing 4,4'-bis(carbomethoxystilbene).

2. Prior Art

Bis(carboalkoxystilbene) derivatives, such as for example 4,4'-bis(carbomethoxystilbene), possess the necessary diester functionality for copolymerization with 4,4'-diol species or α-dihydroxy species via transesterification and subsequent loss of alcohol. Moreover, compounds containing conjugated aromatic rings (e.g., disubstituted stilbene compounds such as 4,4'-bis(carbomethoxystilbene)) fluoresce in the presence of long wave ultraviolet and have been shown to give rise to fluorescent brightening when deposited onto fabric. See H. Hefti in "Fluorescent Whitening Agents", R. Anliker and G. Miller, Eds., George Thieme Publisher, Stuttgart, 1975. Accordingly, it is useful to incorporate such derivatives into copolymers to provide a functionality which fluoresces on the presence of long wave UV light. Block copolymers of this type used in detergent compositions are described in the co-pending application in the name of Langer et al. filed concurrently with this application. The use of these copolymers in detergent compositions is also described in a second co-pending application filed concurrently with this application.

The art teaches many processes for synthesizing bis(carboalkoxystilbene) derivatives. U.S. Pat. No. 4,798,911 to Lentz et al., for example, teaches the dehydrogenation of substituted 1,2-diphenylethanes in the presence of palladium catalysts under forcing conditions. Heitz, et al., *Makromol Chem.*, 189(1), 119 (1988) teaches the coupling of methyl 4-bromobenzoate with ethylene. Both these processes involved the use of costly palladium catalysts which makes the process expensive.

U.S. Pat. No. 4,789,755 et al. teaches the dehydrodimerization of methyl p-toluate with sulfur. In this process, highly toxic hydrogen sulfide is produced as a by-product of the reaction.

U.S. Pat. No. 4,713,472 to Van Sickle teaches a multi-step process starting from methyl 4-formylbenzoate.

None of these methods involves the Wittig reaction which is the basis for the improved methods of the subject invention (G. Wittig and U. Schollkopf, Ber., 87: 1318 (1954)) and instead these processes teach reactions which either utilize costly reagents (such as palladium catalysts) or produce unsafe by-products (such as hydrogen sulfide).

U.S. Pat. No. 4,537,985 to Puskas et al. teaches a Wittig process similar to that of the invention but used for the production of a 1,4 bis[2-(4'-carbomethoxystyrenyl)] benzene.

B. H. Lee and C. S. Marvel, *J. Polymer Sci., Polym. Chem. Ed.*, 20, 393 (1982) teaches a Wittig reaction between (4-carbomethoxy)benzyltriphenyl phosphonium bromide and methyl 4-formylbenzoate in the presence of sodium methoxide which is used for the production of a 4,4'-bis(carboalkoxystilbene) derivative. Unlike the reaction of the invention, this reaction uses potentially carcinogenic methylene chloride as a solvent and requires a phase-transfer reagent.

While there is no technical requirement for the presence of methylene chloride, the use of a phase-transfer agent or the use of costly catalysts during the Wittig reaction applicants are unaware of any process in the art for the production of a 4,4'-bis(carboalkoxystilbene) derivative in which one or more of these is not used.

Thus, there is a need in the art for both a less costly and safer way (i.e., via an improved Wittig process) of preparing a 4,4'-bis(carboalkoxystilbene) derivative.

SUMMARY OF THE INVENTION

The subject invention teaches an improved method for obtaining 4,4'-bis(carboalkoxystilbene) derivatives. In particular, the method is an improved Wittig-type reaction in which potentially carcinogenic solvents ar not required and in which a pure cis or trans form of the final product can be isolated. In addition, the process is less expensive in that the use of a phase-transfer reagent (e.g. tetrabutylammonium iodide) is not required.

DETAILED DESCRIPTION OF THE INVENTION

The present invention teaches a method for producing a 4,4'-bis(carboalkoxystilbene) derivative or derivatives thereof which method comprises:

(a) Reacting Compound I

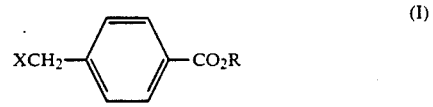

wherein X is a halogen atom such as chlorine, bromine or iodine and;

R is an alkyl group having 1 to 15 carbons, preferably 1-3 carbons, most preferably 1 carbon (i.e., methyl); in the presence of a solvent compound, wherein said solvent is preferably selected from the group of solvents consisting of toluene, benzene, xylene, chloroform, tetrahydrofuran, dioxane, diethyl ether, diphenyl ether or mixtures thereof and further in the presence of $\phi_3 P$ to form compound II:

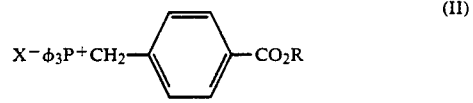

wherein X and R are defined as above; and (b) further reacting compound II with compound III

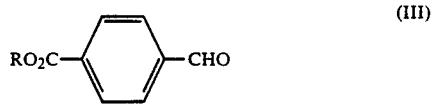

wherein R is defined as above in the presence of a base and solvent; wherein said base is preferably selected from the group of bases consisting of alkali metal alkoxides (having 1-5 carbon atoms), phenoxides, hydrides, alkylates, phenylates, amides, and disilazides; and wherein said solvent is preferably selected from the group consisting of ROH, wherein R is a $C_1$-$C_5$ alkyl group, DMSO, DMF, DMAC, NMP, diethyl ether, dioxane, THF, hexane, benzene, toluene, xylene, or mixtures thereof; in order to obtain a stilbene defined by compound IV

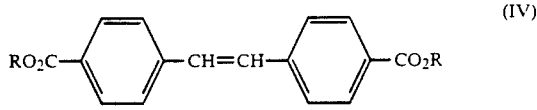

wherein R is defined as above.

In step (a) above, compound I is reacted with a mixture of (1) a compound selected from the group of solvents consisting of toluene, benzene, xylene, chloroform, THF, dioxane, diethyl ether, diphenyl ether or mixtures thereof and (2) $\phi_3P$. The ratio of solvent to $\phi_3P$ may range from 1:1 to 50:1 of $\phi_3P$ to solvent, preferably 1:1 to 5:1 and most preferably 1:1 to 2:1.

In step (b), bases which may be used include alkali metal alkoxides having 1 to 5 carbons such as lithium, sodium, or potassium methoxides or ethoxides, phenoxides, hydrides, alkylates (e.g., methyllithium, butyllithium etc.), phenylates (e.g. phenyllithium), amides (e.g., lithium diethylamide, lithium diisopropyl amide), and disilazides (e.g. potassium hexamethyldisilazide, lithium tetraphenyldimethyldisilazide).

Generally, the length of the alkyl group of the base should correspond to the length of the alkyl group of the ester in the compounds. Thus, for example, if bis(-carbomethoxystilbene) is being made, the base used in step (b) should be an alkali metal methoxide.

Solvents to be used in conjunction with the base in step (b) include solvents selected from the group consisting of ROH, wherein R is an alkyl group having 1 to 5 carbons, dimethyl sulfoxide (DMSO), dimethyl formamide (DMF), dimethyl acetamide (DMAC), N-Methyl-2-pyrrolidinone (NMP), diethyl ether, dioxane, tetrahydrofuran (THF), hexane, benzene, toluene, xylene, or mixtures thereof.

In general, there may be slight excess of compound (II) over compound (III) or of compound (III) over compound (II) and the compounds may be used in a ratio ranging from 1:2 to 2:1.

The base may be used relative to compound (II) or (III) in a range of from 1:1 to 50:1, preferably 1:1 to 5:1, and most preferably 1:1 to 2:1.

The solvent may be used as 1-40% by weight of the solids content of the reaction.

The following examples are intended to illustrate the invention and facilitate its understanding and are not meant to limit it in any way.

EXAMPLE 1

$^1$H and $^{13}$C NMR spectra were obtained on a Varian XL 300 MHz nuclear magnetic resonance spectrometer. Samples were run in $CDCl_3$ with tetramethylsilane as an internal standard. UV absorbance spectra were obtained on a Beckman DU-65 spectrophotometer. Chloroform was used as the sample and reference solvent.

(4-Carbomethoxy)benzyltriphenylphosphonium bromide: To a 2 L 3-neck round bottom flask fitted with a glass stopper, rubber septum, and reflux condenser with a nitrogen inlet tube, was added 64.90 g (283 mmol) methyl 4-bromomethylbenzoate, 81.74 g (311 mmol) triphenylphosphine, and 744 mL toluene. The solution was heated at 80° C. for 5h. After cooling to room temperature, reaction vessel was placed in an ice bath. The resulting precipitate was filtered, washed with toluene, and dried in a vacuum oven to afford 126.35 g (89% (4-carbomethoxy) benzyltriphenylphosphonium bromide) as a white solid. mp.=248°-250° C. (reported in V. Sankaran and C. S. Marvel, J. Polym. Sci, Poly. Chem. Ed , 17, 3949 (1979) as 258°-260° C.): $^1$H NMR ($CDCl_3$, 200 MHz) δ 3.86 (s,3H), 5.70 (d,J=15.3 Hz, 2H), 7.24 (m,4H), 7.71 (m, 15H).

4,4'-Bis(carbomethoxystilbene): To a 2 L 3-neck round bottom flask fitted with a glass stopper, rubber septum, and reflux condenser with a nitrogen inlet tube, was added 126.35 g (251 mmol) (4-carbomethoxy) benzyltriphenylphosphonium bromide, 49.45 g (302 mmol) methyl 4-formylbenzoate, and 632 mL 2:1 methanol:toluene. After the starting material dissolved, 63.2 mL (277 mmol) 25% sodium methoxide solution in methanol was added dropwise over several minutes. The reaction vessel was heated at reflux for 30 minutes. After cooling to room temperature, the reaction vessel was cooled at 0° C. for several hours. The resulting precipitate was filtered and dried in a vacuum oven to afford 59.0 g (79%) 4,4'-bis(carbomethoxy stilbene) as a 7:3 mixture of cis:trans isomers. The isomer mixture was washed several times with 2:1 methanol:toluene solution, dissolving the cis form and leaving the pure trans isomer. The solution was cooled to 0° C. and filtered, affording pure cis isomer.

Cis Isomer mp.=109°-111° C. (reported by B. H. Lee and C. S. Marvel, J. Polym. Sci, Polym. Chem. Ed., 20, 393 (1982) as 109°-111° C.); $^1$H NMR ($CDCl_3$, 200 MHz) δ 3.90 (s, 6H), 6.72 (s, 2H), 7.27 (d, J=8.3 Hz, 4H), 7.90 (d, J=8.3 Hz, 4H); λ max=301 nm; ε=15,700 1/mol-cm.

Trans Isomer mp.=228°-230° C. (reported by B. H. Lee and C. S. Marvel, J. Polym. Sci., Polym. Chem. Ed., 20, 393 (1982) as 227°-228° C.); $^1$H NMR ($CDCl_3$, 200 MHz) δ 3.94 (s, 6H), 7.27 (s, 2H), 7.60 (d, J=8.4 Hz, 4H), 8.05 (d, J=8.4 Hz, 4H); λ max=333 nm; ε=46,600 1/mol-cm.

We claim:

1. A process for the preparation of 4,4'-bis(carboalkoxystilbene) derivatives comprising
   (a) reacting compound I

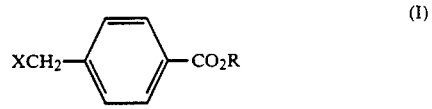

wherein X is halogen atom; and R is an alkyl group having 1-5 carbons;
in the presence of a first solvent compound selected from the group of solvents consisting of toluene, benzene, xylene, chloroform, tetrahydrofuran, dioxane, diethyl ether, diphenyl ether and mixtures thereof;
and in the presence of $\phi_3P$;
to form compound II

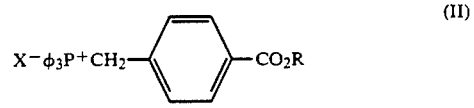

wherein X and R are defined as above;

(b) further reacting compound II with compound III

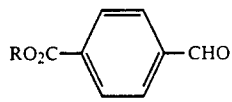
(III)

wherein R is defined as above in the presence of a base and a second solvent;

wherein said base is selected from the group of bases consisting of alkali metal alkoxides having 1 to 5 carbons, phenoxides, hydrides, alkylates, phenylates, amides and disilazides;

and wherein said second solvent is selected from the group consisting of ROH wherein R is a $C_1$-$C_5$ alkyl group, DMSO, DMF, DMAC, NMP, diethyl ether, dioxane, THF, hexane, benzene, toluene, xylene and mixtures thereof;

in order to form an aliphatic stilbene of formula IV

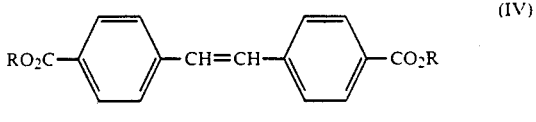
(IV)

wherein R is defined as above.

2. A process according to claim 1, wherein the alkali metal alkoxide base is a lithium, sodium or potassium methoxide or ethoxide.

3. A process according to claim 1, wherein the alkylate base is an alkali metal salt of an $C_1$-$C_{10}$ alkyl group.

4. A process according to claim 1, wherein the phenylate base is an alkali salt of an a phenyl group.

5. A process according to claim 1, wherein the amide base is an alkali metal dialkylamide.

6. A process according to claim 1, wherein the disilazide base is alkali metal hexamethyldisilazide or an alkali metal tetraphenyldimethyldisilazide.

7. A process according to claim 1, wherein the 4,4'-bis(carboalkoxystilbene) is 4,4'-bis(carbomethoxystilbene).

8. A process according to claim 5, wherein the alkali metal dialkylamide is alkali metal diisopropylamide.

* * * * *